(12) United States Patent
Derus et al.

(10) Patent No.: US 6,443,887 B1
(45) Date of Patent: Sep. 3, 2002

(54) SWITCH BASED SPONTANEOUS INFLATION INHIBITOR IN A PUMP FOR AN INFLATION PROSTHESIS

(75) Inventors: Patricia M. Derus, Rogers; Sidney F. Hauschild, Brooklyn Park; Mark Polyak, Minnetonka; George Michael Huepenbecker, Vadnais Heights, all of MN (US)

(73) Assignee: American Medical Systems Inc., Minnetonka, MN (US)

( * ) Notice: Subject to any disclaimer, the term of this patent is extended or adjusted under 35 U.S.C. 154(b) by 0 days.

(21) Appl. No.: 09/749,646

(22) Filed: Dec. 27, 2000

(51) Int. Cl.[7] .................................................. A61F 2/26

(52) U.S. Cl. ........................................ 600/40; 417/441

(58) Field of Search ..................... 600/38–41; 417/305, 417/441, 446, 510

(56) References Cited

U.S. PATENT DOCUMENTS

| | | | |
|---|---|---|---|
| 988,120 A | 3/1911 | Lott | |
| 1,863,057 A | 6/1932 | Innes | |
| 3,312,215 A | 4/1967 | Silber | |
| 3,344,791 A | 10/1967 | Foderick | |
| 3,397,699 A | 8/1968 | Kohl | |
| 3,503,400 A | 3/1970 | Osthagen et al. | |
| 3,642,004 A | 2/1972 | Osthagen et al. | |
| 3,731,670 A | 5/1973 | Loe | |
| 3,797,478 A | 3/1974 | Walsh et al. | |
| 3,812,841 A | 5/1974 | Isaacson | |
| 3,954,102 A | 5/1976 | Buuck | |
| 4,222,377 A | 9/1980 | Burton | |
| 4,267,829 A | 5/1981 | Burton et al. | |
| 4,344,434 A | 8/1982 | Robertson | |
| 4,383,525 A | 5/1983 | Scott et al. | |
| 4,407,278 A * | 10/1983 | Burton et al. ................. | 600/40 |
| 4,453,536 A | 6/1984 | Abild | |
| 4,489,732 A | 12/1984 | Hasson | |
| 4,517,967 A * | 5/1985 | Timm et al. ................. | 600/40 |
| 4,537,183 A | 8/1985 | Fogarty | |
| 4,541,420 A * | 9/1985 | Timm et al. ................. | 600/40 |
| 4,553,959 A | 11/1985 | Hickey et al. | |
| 4,566,446 A | 1/1986 | Fogarty | |
| 4,571,241 A | 2/1986 | Christopher | |
| 4,602,621 A * | 7/1986 | Hakky ......................... | 600/40 |
| 4,619,251 A * | 10/1986 | Helms et al. ................. | 600/40 |
| 4,632,435 A | 12/1986 | Polyak | |
| 4,710,169 A | 12/1987 | Christopher | |
| 4,718,410 A | 1/1988 | Hakky | |
| 4,782,826 A | 11/1988 | Fogarty | |
| 4,791,917 A * | 12/1988 | Finney ........................ | 600/40 |
| 4,850,963 A | 7/1989 | Sparks et al. | |
| 4,932,938 A | 6/1990 | Goldberg et al. | |
| 4,944,732 A | 7/1990 | Russo | |
| 4,958,630 A | 9/1990 | Rosenbluth et al. | |
| 4,968,294 A | 11/1990 | Salama | |
| 5,030,199 A | 7/1991 | Barwick et al. | |

(List continued on next page.)

OTHER PUBLICATIONS

Mulcahy, John J., Another Look at the Role of Penile Prostheses in the Management of Impotence, pp. 169–185 (no date).
Alpha I® Inflatable Penile Prosthesis, Surgical Protocal (Brochure), Mentor, 15 pages (1998).
Mentor Urology Products, (Brochure), Mentor, 21 pages (1998).

Primary Examiner—Eric F. Winakur
Assistant Examiner—Joseph A. Cadugan
(74) Attorney, Agent, or Firm—Jeffrey J. Hohenshell

(57) ABSTRACT

A pump assembly for a penile implant is provided having a mechanism that prevents spontaneous inflation of the cylinders implanted within the patient. The preventative mechanism includes a switching mechanism for moving a valve into either a closed or an open position. When closed, the locking valve prevents fluid flow in an adverse direction. While open, the pump functions normally allowing the cylinders to be inflated.

30 Claims, 4 Drawing Sheets

U.S. PATENT DOCUMENTS

| | | |
|---|---|---|
| 5,034,009 A | 7/1991 | Mouchel |
| 5,041,092 A | 8/1991 | Barwick |
| 5,048,510 A | 9/1991 | Hauschild et al. |
| 5,048,511 A | 9/1991 | Rosenbluth et al. |
| 5,062,417 A | 11/1991 | Cowen |
| 5,063,914 A | 11/1991 | Cowen |
| 5,074,849 A | 12/1991 | Sachse |
| 5,085,650 A | 2/1992 | Giglio |
| 5,088,980 A | 2/1992 | Leighton |
| 5,090,424 A | 2/1992 | Simon et al. |
| 5,112,295 A | 5/1992 | Zinner et al. |
| 5,114,398 A | 5/1992 | Trick et al. |
| 5,131,906 A | 7/1992 | Chen |
| 5,141,509 A | 8/1992 | Burton et al. |
| 5,167,611 A | 12/1992 | Cowan |
| 5,186,180 A | 2/1993 | Bellas |
| 5,230,694 A * | 7/1993 | Rosenblum .................. 600/40 |
| 5,250,020 A | 10/1993 | Bley |
| 5,344,388 A | 9/1994 | Maxwell et al. |
| 5,704,895 A | 1/1998 | Scott et al. |
| 5,851,176 A | 12/1998 | Willard |
| 5,895,424 A | 4/1999 | Steele, Sr. et al. |
| 6,171,233 B1 | 1/2001 | Willard |

* cited by examiner

SWITCH BASED SPONTANEOUS INFLATION INHIBITOR IN A PUMP FOR AN INFLATION PROSTHESIS

CROSS REFERENCE TO RELATED APPLICATIONS

This application is related to patent applications entitled "PRESSURE BASED SPONTANEOUS INFLATION INHIBITOR IN A PUMP FOR AN INFLATABLE PROSTHESIS" and "DIAPHRAGM BASED SPONTANEOUS INFLATION INHIBITOR IN A PUMP FOR AN INFLATABLE PROSTHESIS," which were filed concurrently herewith.

BACKGROUND OF THE INVENTION

This invention generally relates to a pump for inflating a prostheses and more particularly to a pump and valve assembly including a switch actuated valve that inhibits spontaneous inflation of the prosthesis.

One common treatment for male erectile dysfunction is the implantation of a penile prosthesis. Such a prosthesis typically includes a pair of inflatable cylinders that are fluidly connected to a fluid (typically liquid) reservoir via a pump and valve assembly. The two cylinders are normally implanted into the corpus cavernosae of the patient and the reservoir is typically implanted in the patient's abdomen. The pump assembly is implanted in the scrotum. During use, the patient actuates the pump and fluid is transferred from the reservoir through the pump and into the cylinders. This results in the inflation of the cylinders and thereby produces the desired penis rigidity for a normal erection. Then, when the patient desires to deflate the cylinders, a valve assembly within the pump is actuated in a manner such that the fluid in the cylinders is released back into the reservoir. This deflation then returns the penis to a flaccid state.

With inflatable penile prostheses of current designs, spontaneous inflation of the cylinders is known to occasionally occur due to inadvertent compression of the reservoir, resulting in the undesired introduction of fluid into the cylinders. Such inadvertent inflation can be uncomfortable and embarrassing for the patient. This undesirable condition is further described below with reference to a particular prosthetic design.

With reference to FIG. 1, a known pump and valve assembly 8 for use in a penile prosthesis includes a fluid input 10 that is coupled at one end to a reservoir (not shown) and to a housing 12 at its opposite end. Also connected to the housing 12 is a fluid output 14 which, in turn, is connected at its other end to a pair of cylinders (not shown). Linking the fluid input 10 and the fluid output 14 to each other is a common passageway 33, which itself contains a valve assembly that is described in greater detail below. Common passageway 33 is also in fluid communication with a pump bulb 18 that is used to move fluid from the reservoir (not shown) to the cylinders (not shown) in order to inflate the cylinders. The valve assembly located within common passageway 33 includes a reservoir poppet 20 which is biased against a valve seat 24 by a spring 28 and a cylinder poppet 22 which is biased against a valve seat 26 by a spring 30. The springs 28 and 30 are sized so as to keep the reservoir poppet 20U and the cylinder poppet 22 biased against each respective valve seat 24 and 26 under the loads that are encountered when the reservoir is pressurized to typical abdominal pressures.

When the patient wishes to inflate the cylinders, pump bulb 18 is squeezed so as to force fluid from the pump bulb 18 into the common passageway 33. The resulting fluid flow serves to reinforce the force from the spring 28 urging the reservoir poppet 20 against valve seal 24 while at the same time causing compression of the spring 30, and thereby opening cylinder poppet 22. As a result, the fluid travels out through fluid output 14 and into the respective cylinders.

When the patient releases the pump bulb 18 a vacuum is created, thus pulling the poppet 22 back against valve seat 26 (aided by spring 30) and simultaneously pulling the reservoir poppet 20 away from its valve seat 24, against the spring 28. As a result, fluid from the reservoir is thus allowed to flow through the fluid input 10 and into the common passageway 33 passing around the reservoir poppet 20 and into the vacuous pump bulb 18. Once the pump bulb 18 has been filled, the negative pressure is eliminated and the reservoir poppet 20 returns to its normal position. This pumping action of the pump bulb 18 and valve assembly is repeated until the cylinders are[]fully inflated.

To deflate the cylinders, the patient grips the housing 12 and compresses it along the axis of reservoir poppet 20 and cylinder poppet 22 in a manner such that the wall 13 of the housing 12 contacts the protruding end 21 of the reservoir poppet 20 and forces the reservoir poppet 20 away from valve seat 24. This movement, in turn, causes the reservoir poppet 20 to contact cylinder poppet 22 and force cylinder poppet 22 away from valve seat 26. As a result, both poppets 20 and 22 are moved away from their valve seats 24 and 26 and fluid moves out of the cylinders, through the fluid output 14, through common passageway 33, through the fluid input 10 and back into the reservoir. Complete deflation of the cylinders requires the patient to continuously squeeze housing 12 (hence maintaining the valves in an open position) during the entire deflation process. This can present difficulty for patients lacking manual dexterity. Furthermore, there is only limited tactile feedback to the patient through the valve and housing assembly. Thus, the patient does not necessarily know if they are squeezing too hard or not hard enough to facilitate deflation.

Although the springs 28 and 30 are sized to provide sufficient tension to keep poppets 20 and 22 firmly abutted against valve seats 24 and 26 under normal and even somewhat excessive reservoir pressures, it is possible that pressure that exceeds the force provided by the springs. could be exerted upon the reservoir during heightened physical activity or movement by the patient. Such excessive pressure on the reservoir may overcome the resistance of the spring-biased poppets 20 and 22 and thereby cause a spontaneous inflation of the cylinders. After implantation, encapsulation or calcification of the reservoir could occur. The encapsulation could lead to a more snugly enclosed reservoir, at least temporarily thus increasing the likelihood of spontaneous inflation.

BRIEF SUMMARY OF THE INVENTION

The present invention includes a, pump assembly having a triple poppet arrangement wherein the poppets act as valves, such as check valves or flow valves. The cylinder poppet and the reservoir poppet are spring-biased against a valve seat, and under normal circumstances, only allows positive fluid flow when a pump bulb is compressed, thus causing an increase in fluid pressure Which is transferred to the inflatable cylinders. These two poppets function very similarly to those described with reference to the related art pump. assembly, illustrated in FIG. 1.

In addition, a switch actuated poppet is provided between the input from the reservoir and the reservoir poppet. The switch actuated poppet is coupled to a rotor and a spring loaded pusher. The spring loaded pusher is positioned adjacent the wall of the housing so that the patient can easily manipulate it, by compressing the outer wall. The interaction of the spring loaded pusher and the rotor act as an "on-off" type switch; much like the locking mechanism in a ball point pen. Namely, with each actuation of the spring loaded pusher, the switch actuated poppet is moved from .one position to another. A momentary single squeeze moves the switch actuated poppet to either a closed position, where it forms a fluid tight seal preventing fluid flow from the reservoir towards the reservoir poppet; or to an open position wherein such fluid flow is permitted.

The switch actuated poppet is easy to operate and requires little force to be applied by the patient, thus permitting one handed operation. In addition, the positive actuation of the switching mechanism. provides a clicking sound and a perceivable tactile sensation that indicates movement and locking of the mechanisms. This simply provides some feedback to the patient, indicating a successful actuation of the switch.

The switch actuated poppet includes a locking arm that engages the reservoir poppet when the switch actuated poppet is in a closed position. When so engaged, the reservoir poppet and the cylinder poppet are caused to be opened and maintained in that position. This will allow fluid flow from the cylinders (opening the switch actuated poppet) into the reservoir during deflation. The locking mechanism will keep the switch actuated poppet in the closed position at all other times. Should an over pressurization situation occurs, the increase pressure acts to further seal the switch actuated poppet thus, spontaneous inflation is prevented.

To inflate the cylinders, the mechanism is actuated by compressing the housing. This forces the spring loaded pusher to engage the rotor moving it. to its alternate position. In so doing, the switch actuated poppet is withdrawn from its valve seat. In addition, the reservoir poppet and cylinder. poppet are each allowed to close. At this point, the device works just as described with reference to FIG. 1. A single compression of the pump bulb opens the cylinder poppet and forces fluid into the cylinders. As the pump bulb expands, the vacuum forces generated open the reservoir poppet and draw fluid from the reservoir.

When it is desired to deflate the cylinders, the switch is actuated again, causing switch actuated poppet to move to a sealing position. Since the reservoir poppet and cylinder poppet are forced open, deflation can occur. Once complete, the switch actuated poppet (in its closed position) prevents fluid from moving from the reservoir to towards the cylinders, even during an overpressurization situation.

DETAILED DESCRIPTION OF THE INVENTION

Figure 1:
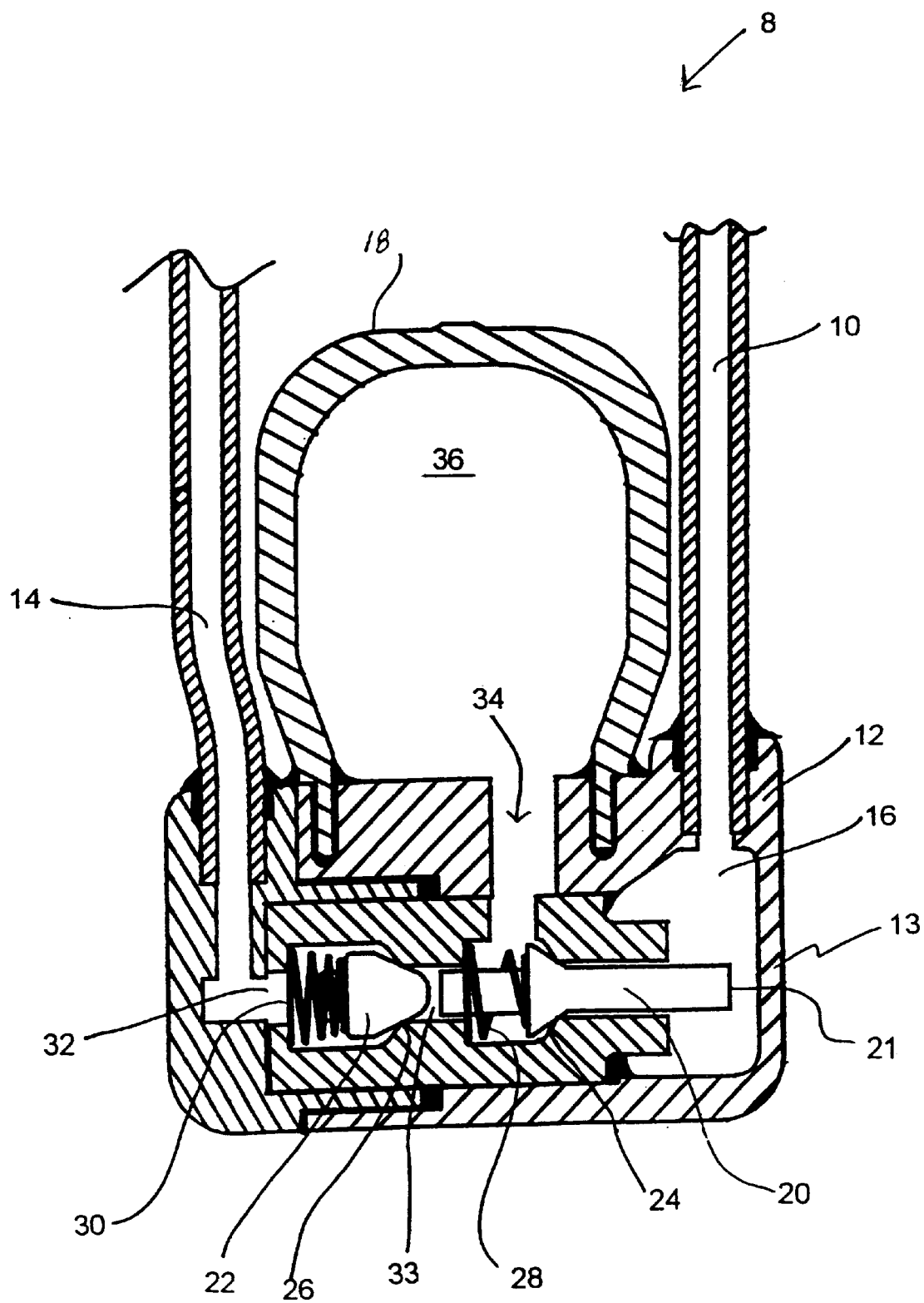
FIG. 1 is a side-sectional view of a penile pump according to the teachings of the related art.

Referring to FIG. 1, a pump assembly is shown and generally referred to as 8. The pump assembly 8, as illustrated in FIG. 1, is essentially that of the related art, but an understanding of the working elements of pump assembly 8, as illustrated in FIG. 1, is beneficial to understanding the operation of the embodiment of the present invention. Generally, the pump assembly 8 will be implanted into the patient's scrotum. A separate fluid-filled reservoir (not shown) is implanted in some other portion of the patient's body, usually in the abdomen. Fluidly connecting the reservoir to the pump assembly 8 is fluid input 10, which will usually be a flexible silicone tube. A pair of inflatable cylinders (not shown) are usually implanted in the patient's corpus cavernosae and are fluidly connected to pump assembly 8 via fluid output 14, which is also usually a flexible silicone tube.

In general, when pump assembly 8 is actuated, fluid is drawn from the reservoir through the pump assembly 8 and pumped into the cylinders. During the inflation process and until released by the patient, the pump assembly 8 maintains the fluid pressure in the cylinders, thus keeping them in their inflated state. When deflation is desired, the patient manipulates assembly 8, permitting fluid to transfer out of the inflatable cylinders and into the reservoir, thereby deflating the cylinders and returning them to a flaccid state.

Pump assembly 8 generally includes a housing 12 usually formed of silicone. Attached to housing 12 is a pump bulb 18, which includes a relatively large pump chamber 36. Fluid input 10 is coupled to the housing 12 and empties into a reservoir chamber 16. As such, fluid input 10 couples reservoir chamber 16 to the reservoir. A common passageway 33 is fluidly coupled to reservoir chamber 16 at one end of the housing 12, and is fluidly coupled to fluid output 14 at an opposite end of the housing 12. Similarly, the pump chamber 36 is fluidly coupled to the common passageway 33 via pump passageway 34.

Disposed within common passageway 33 is a reservoir poppet 20, which functions as a check valve. Reservoir poppet 20 is an elongated member having a contoured portion, which abuts reservoir poppet valve seat 24 forming a fluid tight seal. A reservoir poppet spring 28 engages reservoir poppet 20 and biases reservoir poppet 20 against the reservoir poppet valve seat 24. Also disposed within common passageway 33 and in line with reservoir poppet 20 is cylinder poppet 22. Cylinder poppet 22 forms a second check valve within common passageway 33. Cylinder poppet 22 is biased by cylinder poppet spring 30 against cylinder poppet valve seat 26 in a normal state, thereby forming another fluid tight seal within common passageway 33. Reservoir poppet 20 is substantially longer than cylinder poppet 22. A front end of reservoir poppet 20 extends into reservoir chamber 16, in close proximity to an outer wall of housing 12. Furthermore, the front end of cylinder poppet 22 is in close proximity to the rear end of reservoir poppet 20. As such, the patient can manipulate both poppets 20 and 22 by compressing: the wall of housing 12. Compression of the housing 12 will cause the reservoir poppet 20 to compress reservoir poppet spring 28 thus displacing the reservoir poppet 20 from reservoir poppet valve seat 24. This motion will also cause cylinder poppet 22 to be displaced from cylinder poppet valve seat 26 while compressing cylinder poppet spring 30. When both reservoir poppet 20 and cylinder poppet 22 are displaced from their respective valve seats, fluid is allowed to freely flow between reservoir chamber 16 and fluid output 14, and hence fluid is allowed to freely flow between the reservoir and the cylinders.

During a majority of the time, pump assembly 8 will be in the configuration shown in FIG. 1. That is, both reservoir poppet 20 and cylinder poppet 22 are abutting their respective valve seats 24 and 26, forming a fluid tight seal. When inflation is desired, pump bulb 18 is manually compressed by the patient. This forces the fluid in pump chamber 36 out through pump passageway 34 and into common passageway 33, under relatively high pressure. Because of the location of pump passageway 34 with respect to the reservoir poppet 20, this increased pressure causes reservoir poppet 20 to further abut reservoir poppet valve seat 24. This increased pressure is more than sufficient to remove cylinder poppet 22 from its abutment with cylinder poppet valve seat 26, by compressing cylinder poppet spring 30. As such, the pressurized fluid is allowed to pass through a portion of the common passageway 33 and into fluid output 14, where it eventually reaches an inflatable cylinder. When released, the pump bulb 18 expands back to its original configuration, creating negative pressure within pump chamber 36 and common passageway 33. This negative pressure draws cylinder poppet 22 towards valve seat 26 and simultaneously pulls reservoir poppet 20 away from valve seat 24. As such, fluid is drawn from the reservoir, and into pump chamber 36 until the negative pressure is eliminated. Then, reservoir poppet spring 28 causes the reservoir poppet 20 to reseat itself against valve seat 24.

Repeated compression of pump bulb 18 eventually inflates the cylinders to a sufficient degree of rigidity for the patient. Once inflated, the fluid remaining in fluid output 14 is under a relatively high degree of pressure. This high pressure fluid aids cylinder poppet spring 30 in forcing cylinder poppet 22 against cylinder poppet valve seat 26 again forming a fluid tight seal and preventing fluid from within the cylinders from passing through (preventing deflation of the cylinders).

When the patient desires deflation of the cylinders, the wall of housing 13 is manually compressed. This compression forces reservoir poppet 20 away from reservoir poppet valve seat 24 and simultaneously causes cylinder poppet 22 to be removed from cylinder poppet valve seat 26. The pressurized fluid within the cylinders and fluid output 14 naturally returns to the reservoir via common passageway 33. Furthermore, the cylinders can be manually compressed forcing out any remaining fluid. Once the cylinders are satisfactorily emptied, the patient releases the grip on housing 12, thus allowing cylinder poppet 22 and reservoir poppet 20 to once again abut their respective valve seats 24 and 26.

As described above, pump assembly 8 (as shown in FIG. 1) works relatively well under normal circumstances. However, when the reservoir is inadvertently compressed through normal body movement or capsule formation, the pressure generated may be sufficient to remove reservoir poppet 20 and cylinder poppet 22 from their respective valve seats 24 and 26, thus spontaneously inflating the cylinders. When sufficient force is generated against the reservoir (or a similar component) to cause the fluid pressure to exceed the resistive characteristics of poppets 20 or 22, an overpressure situation has occurred. Of course, the only way. to release this spontaneous inflation is to manually release the check valves.

Figure 2:
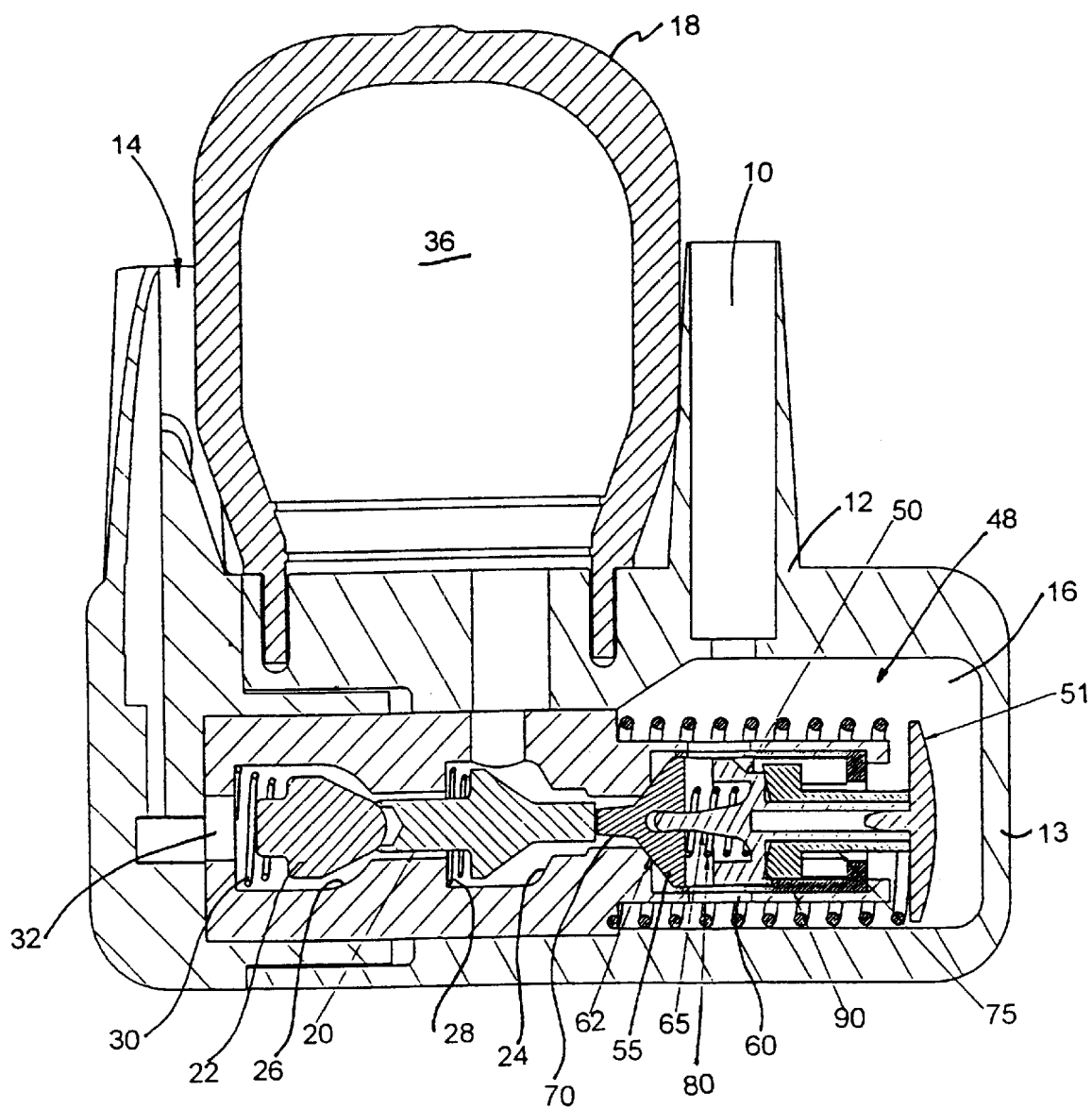
FIG. 2 is a partial side-sectional view of a penile pump utilizing a switch actuated poppet in the closed position.
Figure 3:
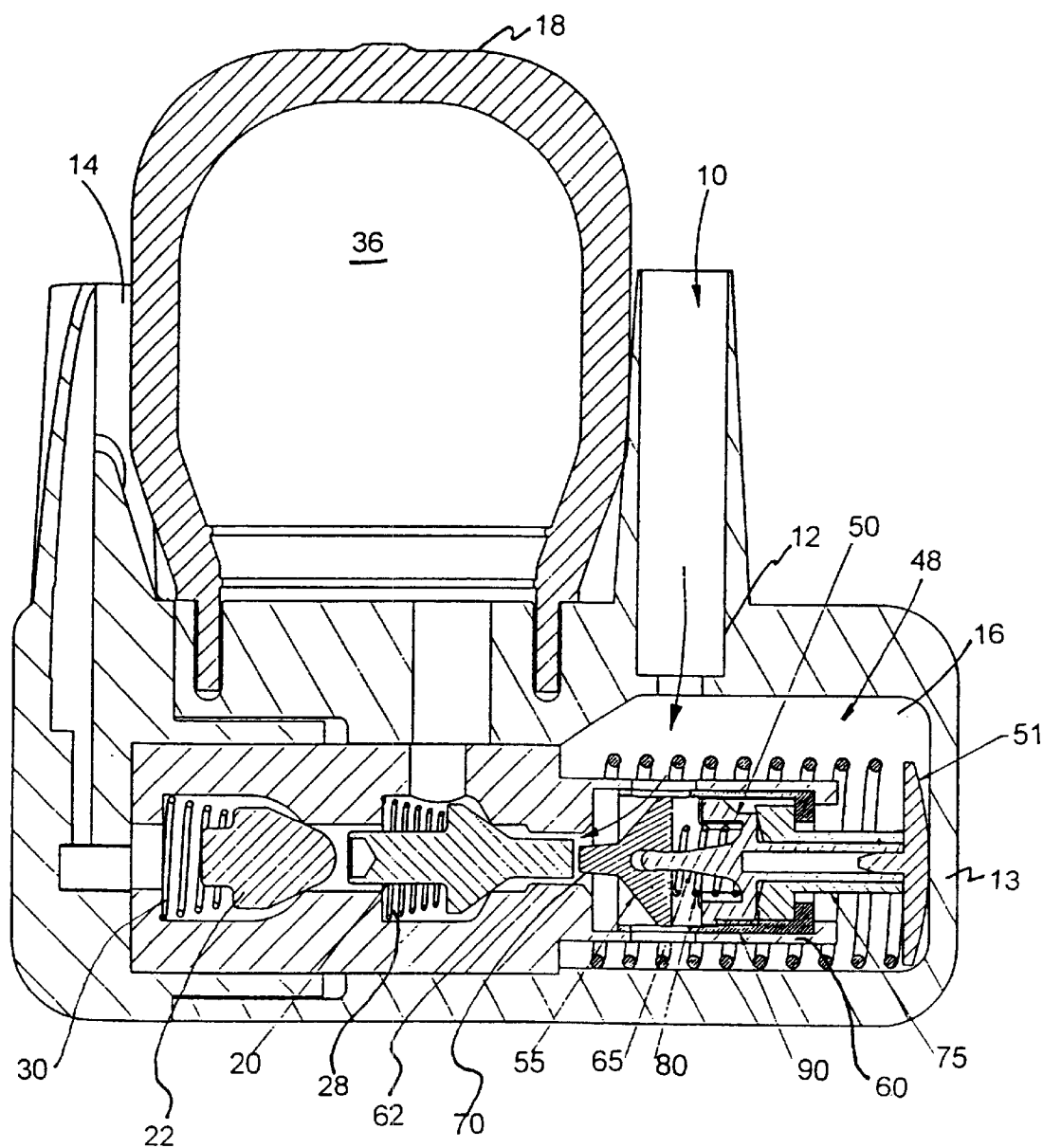
FIG. 3 is a partial side-sectional view of the penile pump shown in FIG. 2 wherein the switch actuated poppet is locked into an open position.

Referring to FIGS. 2 and 3, the preferred embodiment of the present invention is shown and described. Reservoir poppet 20 and cylinder poppet 22 are spring biased towards their respective valve seats 24, 26 (biased to move from left to right as illustrated). A switch mechanism 48 is positioned between reservoir poppet 20 and fluid input 10. Switch mechanism 48 includes a switch actuated poppet or locking poppet 55 that selectively engages valve seat 62 to provide a fluid tight seal. Locking poppet 55 is moveably coupled to a rotor 50 by a front shaft 65 and a biasing spring 80. Locking poppet 55 is a floating, self-aligning valve. That is, due to its moveable coupling with front shaft 65 and its tapered configuration, locking poppet 55 will naturally seek to form a seal as it is allowed to abut valve seat 62. In FIG. 2, locking poppet 55 is shown in a closed position where it engages valve seat 62 in a fluid tight manner. Biasing spring 80 acts to keep locking poppet 55 in this position, unless sufficient force is generated on the opposite side of locking poppet 55 (i.e., deflation of the cylinders). Should this occur, biasing spring 80 compresses and locking poppet 55 slides along a portion of front shaft 65, while rotor 50 remains fixed in place.

Rotor 50 is coupled to a spring loaded pusher 75, that terminates in thumb cap 51, which is adjacent a wall 13 of housing 12. Rotor 50 and spring loaded pusher 75 are partially enclosed within a switch housing 60 that includes stator 90 having a plurality of cams and grooves (described in greater detail below). Thus, each time spring loaded pusher 75 is actuated, rotor 50 moves within stator 90 and switch housing 60. The configuration of the cams and grooves cause rotor 50 to alternatively lock between two possible positions (open in FIG. 3 and closed in FIG. 2). This mechanism functions in a well known manner similar to that of a ball point pen.

With each actuation of rotor 50, locking poppet 55 is moved between an open and a closed position. In the open position, fluid is allowed to freely flow through locking poppet 55, to and from the reservoir. In the closed position, fluid may only flow into the reservoir. Biasing spring 80 acts to keep locking poppet 55 sealed, once placed in the closed position. Any pressure generated on the reservoir side of poppet 55 simply supplements the force of biasing spring 80, causing locking poppet to be more firmly held in place. Note that in this position, rotor 50 does not .necessarily "lock" the locking poppet in the closed position, but rather accommodates the function of biasing spring 80.

The patient will normally keep the pump assembly 8 in the position illustrated in FIG. 2. Namely, locking poppet 55 is in the closed position. An extension arm 70 attached to locking poppet 55 engages reservoir poppet 20, causing it to open. This action in turn opens cylinder poppet 22. If the cylinders are inflated, they can be deflated when assembly 8 is in this configuration (with locking poppet 55 in the closed position). That is, the pressure generated by the fluid within the cylinder (alone or because of manual compression) will work against locking poppet 55. This will cause biasing spring 80 to compress, allowing locking poppet 55 to open somewhat by sliding along front shaft 65. Fluid is then able to return to the reservoir. Once the cylinders have been emptied, locking poppet 55 will remain in the closed position, preventing spontaneous inflation. Any fluid remaining will be retained within pump bulb 18 due to the vacuum forces generated. A compression of pump bulb 18 will either cause a minimal amount of fluid to enter the cylinder, or more likely will cause that fluid to open locking poppet 55 and enter the reservoir. If fluid enters the cylinders, it will immediately return to pump bulb 18 when pump bulb 18 re-expands. If the fluid enters the reservoir, the vacuum forces will retain pump bulb 18 in a compressed state. In either event, spontaneous inflation is not facilitated.

When the patient desires to inflate the cylinders, housing 12 is compressed causing spring loaded pusher 75 to actuate rotor 50 and move locking poppet 55 into the open position as illustrated in FIG. 3. Extension arm 70 no longer engages reservoir poppet 20, hence both reservoir poppet 20 and cylinder poppet 22 are biased to their closed positions.

Subsequently, as the patient compresses pump bulb 18 fluid is forced to open cylinder poppet 22 (and retain reservoir poppet 20 in a closed position) and inflate the cylinders. Releasing pump bulb 18 generates vacuum forces that close cylinder poppet 22 and open reservoir poppet 20. Fluid is then drawn from the reservoir into pump bulb 18. Since locking poppet 55 is locked into the open position, it does not hinder this process. While the cylinders are inflated, locking poppet 55 should remain in the open position. This allows reservoir poppet 20 and cylinder poppet 22 to function just as described with reference to FIG. 1. As described above, when deflation is desired, housing 12 is again compressed which causes locking poppet 55 to move the closed position of FIG. 2.

One consideration in the configuration of switch mechanism 48 is the distance of travel felt by the operator. Specifically, as housing 12 is compressed, pusher 75 is moved a certain distance to effectuate the switching action. The amount of travel must be long enough so that the operator feels the movement and can tell that the action has been completed. On the other hand, this distance cannot be too long, otherwise the size of the components would be too large to be practical. If the distance is too small, the operator may have difficulty operating switch mechanism 48. These components need to be sized so that they can be manufactured at a reasonable cost. Thus, their size cannot be too small, otherwise the precision required during manufacturing becomes too complex to be cost effective.

Figure 4:
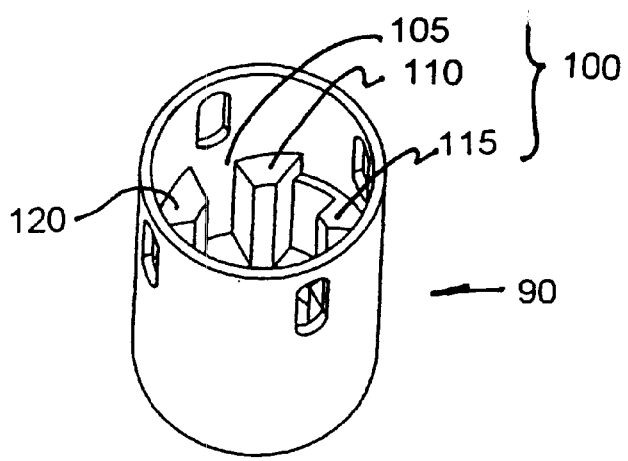
FIG. 4 is a perspective view of a stator.
Figure 5:
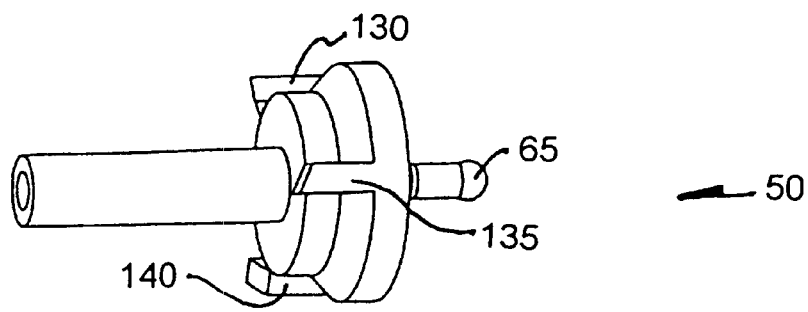
FIG. 5 is a perspective view of a rotor.
Figure 6:
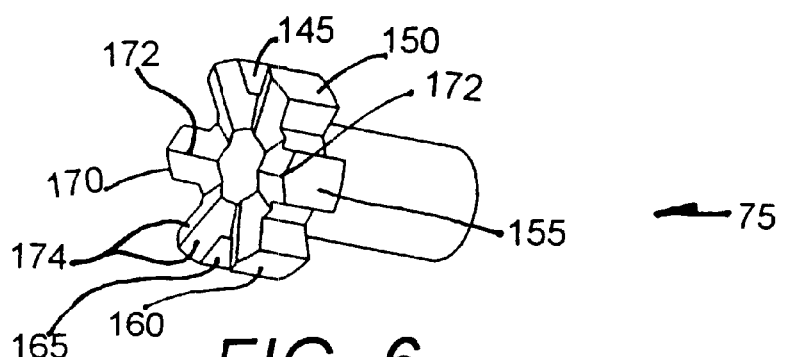
FIG. 6 is a perspective view of a pusher.

Therefore, what is desired is a configuration having relatively small but easily manufactured components that result in a sufficiently long travel distance for switch 48. One such configuration is illustrated by FIGS. 4–6. Here stator 90, rotor 50, and pusher 75 are shown in a perspective view. Stator 90 includes three substantially similar sets of cams and channels. First cam set 100 is illustrated and includes channel 105, first cam 110 and second cam 115. The second cam set is not visible, while a portion of third cam set 120 is. Rotor 50 includes a number of angled cam riders having beveled surfaces. Specifically, first cam rider 130, second cam rider 135 and third cam rider 140 are provided around rotor 50. Pusher 75 has six cam lifting surfaces designated cam lifters 145, 150, 155, 160, 165, and 170. Each cam lifter 145, 150, 155, 160, 165, 170 has a medial ridge 172 with a beveled edge 174 on each side thereof.

When assembled as in FIGS. 2 and 3, the interaction of stator 90, rotor 50 and pusher 75 results in a movement having a desirable length of travel. Referring to FIGS. 2–6, the operation of switch mechanism 48 is illustrated. As housing wall 12 is compressed, thumb cap 51 is caused to move, which in turn causes pusher 75 to move to the left (as illustrated in FIGS. 2 & 3). As this occurs, three of the six cam lifters 145 will engage the angled cam riders 130, 135, and 140. Rotor 50 will, as a whole, be moved to the left. When rotor 50 is moved toward the left, it will be caused to disengage the particular set of cams or channels (i.e., 105 or 115) it was previously in contact with. At the same time, due to the angled surfaces contacting one another on both pusher 75 and rotor 50, rotor 50 will be caused to rotate. As this rotation occurs the various cam riders 130,135, 140 will be caused to alternate between contact with a given cam (i.e., 110, 115) and a given channel (i.e., 105), due to the illustrated configuration of the cam sets 100, 120. In other words, with each actuation of switch mechanism 48, rotor 50 will move from its current position to the next sequential position.

Thus, if rotor 50 is being held towards its left most position (as in FIG. 2) via contact between a given cam rider 130, 135, 140 and a given cam (i.e., 110, 115), subsequent actuation will cause rotor 50 to move further towards the left, disengage the cam (i.e., 110, 115) and rotate. When released, cam riders 130, 135, 140 will be aligned with channels (i.e., 105) within stator 90. Thus, rotor 50 will move toward the right, along with pusher 75, as both are biased by spring 80. The configuration of FIG. 3 is thereby achieved. Each actuation of switch mechanism 48 will cause movement between the position illustrated in FIG. 2 to the position illustrated in FIG. 3, or vice versa.

By providing a two position switch mechanism 48 in conjunction with the traditional reservoir and cylinder poppets 20,22, several advantages are realized. Switch mechanism 48 provides a positive indication to the patient as it is moved from one position to the other, thereby aiding the patient in its proper use. The patient only has to apply a single, momentary squeeze to deflate the cylinders. Spontaneous inflation is prevented because any overpressure generated while locking poppet 55 is in the closed position will serve to further seal it, rather than opening it. Finally, by being able to effectively remove locking poppet 55 from the process (in the open position), easy inflation of the cylinders is facilitated. These features can be provided in pump assembly 8 having the same general size as the related art devices and from the patient's perspective operate in the same easy manner.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. For example, it is contemplated as part of the invention to use the various mechanisms disclosed herein in numerous types of fluid-filled and controlled prosthesis, including, e.g., penile prosthesis and artificial urinary sphincters. Accordingly, the present invention is not limited in the particular embodiments that have been described in detail therein. Rather, reference should be made to the appended claims as indicative of the scope and content of the present invention.

What is claimed is:

1. A pump assembly for an implantable prosthesis, comprising:
    a housing having a fluid passageway, the fluid passageway having an inlet and an outlet;
    a first flow valve located within the fluid passageway between the inlet and the outlet; and
    a switchable member located within the housing that selectively operates in a first predetermined mode that substantially seals a portion of fluid passageway between the first flow valve and the inlet or a second predetermined mode, the switchable member including a rotator and a stator, wherein one of the rotator and stator includes a cam rider and the other of the rotator and stator includes a cam and a channel.

2. The pump assembly of claim 1 wherein fluid pressure within the inlet serves to further seal the switch mechanism when in the first predetermined mode.

3. The pump assembly of claim 1, further comprising a second flow valve located within the fluid passageway.

4. The pump assembly of claim 1, wherein the switchable member has an open and a closed position.

5. The pump assembly of claim 1, wherein the switchable member further includes:
    a locking valve moveable between an open and closed position, wherein the locking valve seals the portion of the fluid passageway when in the closed position.

6. The pump assembly of claim 5, wherein the locking valve is a floating self aligning locking valve.

7. The pump assembly of claim 5, wherein the rotor is operatively coupled to the locking valve so that linear movement of the rotor causes the rotor to move between a first locked position and a second locked position, wherein the first locked position corresponds to an open position of the locking valve and the second locked position corresponds to the closed position of the locking valve.

8. The pump assembly of claim 7, further including:
a spring loaded pusher coupled to the rotor and placed adjacent to a wall of the housing so that selective engagement of the wall of the housing will cause the spring loaded pusher to engage and actuate the rotor.

9. The pump assembly of claim 1, wherein the switchable member is a spring loaded valve that only allows fluid flow in one direction when in the first predetermined mode and allows bidirectional fluid flow when in the second predetermined mode.

10. A pump assembly for an implantable prosthesis comprising:
a housing having a fluid passageway, the fluid passageway having an inlet and an outlet;
a first flow valve located within the fluid passageway between the inlet and the outlet;
a switchable member located within the housing that selectively operates in a first predetermined mode that substantially seals a portion of fluid passageway between the first flow valve and the inlet or a second predetermined mode,
a locking valve moveable between an open and closed position, wherein the locking valve seals the portion of the fluid passageway when in the closed position,
a rotor operatively coupled to the locking valve so that linear movement of the rotor causes the rotor to move between a first locked position and a second locked position, wherein the first locked position corresponds to an open position of the locking valve and the second locked position corresponds to the closed position of the locking valve, and
a pusher having a plurality of cam lifters, wherein each cam lifter includes a medial ridge with a beveled edged on each side thereof.

11. The pump assembly of claim 10 wherein the pusher has six cam lifters.

12. The pump assembly of claim 10 wherein said rotor further includes:
a plurality of cam riders, each cam rider having a beveled terminating surface for selectively engaging one of the plurality of cam lifters of the pusher so that linear movement of the pusher produces linear and rotational movement of the rotor.

13. The pump assembly of claim 12, further comprising:
a stator having a plurality of sets of cams and channels, wherein each channel is configured to selectively receive one of the cam riders and each cam is configured to selectively support one of the cam riders.

14. The pump assembly of claim 13, wherein the pusher, the stator, and the rotor are configured to interact so that as the pusher is linearly moved a predetermined distance against the rotor, the rotor is linearly moved and caused to rotate so that the plurality of cam riders are caused to move within the stator.

15. The pump assembly of claim 14, wherein the predetermined distance is sufficient to allow an operator to sense the movement.

16. The pump assembly of claim 13, wherein the pusher, the stator; and the rotor are configured to interact so that as the pusher is moved a predetermined distance against the rotor, the rotor is moved and caused to rotate so that the plurality of cam riders are caused to move within the stator.

17. A penile prosthesis comprising:
a housing;
a fluid inlet to the housing, coupleable to a reservoir;
a fluid outlet from the housing, coupleable to an inflatable cylinder;
a fluid passageway coupling the inlet to the outlet;
a reservoir chamber coupling the inlet to the fluid passageway;
a first check valve disposed within the fluid passageway and biased towards a closed position;
a second check valve disposed within the fluid passageway between the first check valve and the reservoir chamber and biased towards a closed position;
a pump bulb in fluid communication with the fluid passageway between the first and second check valves;
a locking valve disposed between the second check valve and the reservoir chamber and switchable between an open position and closed position, wherein the locking valve seals the fluid passageway between the locking valve and the second check valve,
a switching mechanism coupled to the locking valve to selectively move and lock the locking valve into either the open or the closed position, the switching mechanism comprising a rotor coupled to the locking valve and a spring loaded pusher coupled to the rotor,
a stator, and
wherein linear actuation of the spring loaded pusher causes the rotor to move between a first position and a second position.

18. The prosthesis of claim 17, wherein when the locking valve is in the closed position the locking valve can allow fluid flow from the outlet towards the reservoir but cannot allow fluid flow from the reservoir towards the outlet.

19. The prosthesis of claim 17 wherein the rotor includes a plurality of cam riders, and the switching mechanism includes the stator with a plurality of cams and channels.

20. The prosthesis of claim 17, further including an arm coupled to the locking valve, wherein the arm engages and opens the second check valve, which opens the first check valve, when the locking valve is in the closed position.

21. The prosthesis of claim 17, wherein the locking valve is a floating, self aligning locking valve.

22. A penile prosthesis comprising:
a housing;
a fluid inlet to the housing, coupleable to a reservoir;
a fluid outlet from the housing, coupleable to an inflatable cylinder;
a fluid passageway coupling the inlet to the outlet;
a reservoir chamber coupling the inlet to the fluid passageway;
a first check valve disposed within the fluid passageway and biased towards a closed position;
a second check valve disposed within the fluid passageway between the first check valve and the reservoir chamber and biased towards a closed position;
a pump bulb in fluid communication with the fluid passageway between the first and second check valves; and
a locking valve disposed between the second check valve and the reservoir chamber and switchable between an open position and closed position, wherein the locking valve seals the fluid passageway between the locking valve and the second check valve, a switching mechanism coupled to the locking valve to selectively move and lock the locking valve into either the open or the closed position, wherein the switching mechanism includes:
 a rotor coupled to the locking valve; and
 a pusher having a plurality of cam lifters, wherein each cam lifter includes a medial ridge with a beveled edged on each side thereof.

23. The pump assembly of claim 22 wherein the pusher has six cam lifters.

24. The pump assembly of claim 22 wherein said rotor further includes:

a plurality of cam riders, each cam rider having a beveled terminating surface for selectively engaging one of the plurality of cam lifters of the pusher so that linear movement of the pusher produces linear and rotational movement of the rotor.

25. The pump assembly of claim 24, further comprising:

a stator having a plurality of sets of cams and channels, wherein each channel is configured to selectively receive one of the cam riders and each cam is configured to selectively support one of the cam riders.

26. The pump assembly of claim 25, wherein the pusher, the stator, and the rotor are configured to interact so that as the pusher is linearly moved a predetermined distance against the rotor, the rotor is linearly moved and caused to rotate so the plurality of cam riders are caused to move within the stator.

27. The pump assembly of claim 26, wherein the predetermined distance is sufficient to allow an operator to sense the movement.

28. A method of preventing inadvertent inflation of an implantable prosthetic comprising the steps of:

providing a pump assembly comprising a housing having a fluid passageway, the fluid passageway having an inlet and an outlet; a first flow valve located within the fluid passageway between the inlet and the outlet; and a switchable member located within the housing that selectively operates in a first predetermined mode that substantially seals a portion of fluid passageway between the first flow valve and the inlet or a second predetermined mode, the switchable member including a rotator and a stator, wherein one of the rotator and stator includes a cam rider and the other of the rotator and stator includes a cam and a channel;

setting a position of a locking valve to a closed position to prevent fluid flow in a direction causing inadvertent inflation, during periods of non-use; and setting the locking valve to an open position to allow free flow of fluid during periods of use.

29. The method of claim 28, wherein the step of setting the positions of the locking valve include actuating the switchable member.

30. The method of claim 28, wherein the step of setting the positions of the locking valve include locking the locking valve into either the closed position or the open position.

* * * * *